(12) United States Patent
Dutta et al.

(10) Patent No.: US 9,927,395 B1
(45) Date of Patent: Mar. 27, 2018

(54) MINIATURIZED GAS SENSOR DEVICE AND METHOD

(71) Applicant: Ohio State Innovation Foundation, Columbus, OH (US)

(72) Inventors: Prabir K. Dutta, Worthington, OH (US); Suvra P. Mondal, Tripura (IN)

(73) Assignee: Ohio State Innovation Foundation, Columbus, OH (US)

(*) Notice: Subject to any disclaimer, the term of this patent is extended or adjusted under 35 U.S.C. 154(b) by 0 days.

(21) Appl. No.: 15/783,812

(22) Filed: Oct. 13, 2017

Related U.S. Application Data

(60) Continuation of application No. 15/693,266, filed on Aug. 31, 2017, which is a division of application No. 14/212,006, filed on Mar. 14, 2014.

(60) Provisional application No. 61/801,106, filed on Mar. 15, 2013.

(51) Int. Cl.
*G01N 7/00* (2006.01)
*G01N 21/00* (2006.01)
*G01N 27/00* (2006.01)
*G01N 27/417* (2006.01)
*G01N 33/00* (2006.01)

(52) U.S. Cl.
CPC ....... *G01N 27/417* (2013.01); *G01N 33/0031* (2013.01); *G01N 33/0037* (2013.01)

(58) Field of Classification Search
CPC .......... G01N 7/00; G01N 21/00; G01N 27/00; G01N 31/00; G01N 33/00; G01N 27/26
USPC ...... 422/83, 98; 436/43, 106, 116, 117, 118; 73/23.2; 204/421, 424, 431, 196.09
See application file for complete search history.

(56) References Cited

U.S. PATENT DOCUMENTS

| 4,294,679 A | 10/1981 | Maurer et al. |
| 5,071,526 A | 12/1991 | Pletcher et al. |
| 5,841,021 A | 11/1998 | De Castro et al. |
| 6,277,267 B1 | 8/2001 | Geloven et al. |
| 6,663,756 B2 | 12/2003 | Lee et al. |
| 9,164,080 B2 | 10/2015 | Dutta et al. |

(Continued)

FOREIGN PATENT DOCUMENTS

| KR | 100843169 B1 | 7/2008 |
| WO | 2009049091 A2 | 4/2009 |

OTHER PUBLICATIONS

Gad-El-Hak, "MEMS Design and Fabrication," The MEMS Handbook, Second Edition, 2006, Taylor & Francis Group, LLC, pp. 1-15.

(Continued)

*Primary Examiner* — Brian J. Sines
(74) *Attorney, Agent, or Firm* — Meunier Carlin & Curfman LLC

(57) ABSTRACT

Various embodiments of a gas sensor device and method of fabricating a gas sensor device are provided. In one embodiment a gas sensor device includes a base substrate, an electrolyte layer disposed on the base substrate and a plurality of potentiometric sensor units electrically coupled to the base substrate. Each potentiometric sensor unit includes an electrolyte layer disposed on the base substrate, a sensing electrode comprising tungsten oxide ($WO_3$) and platinum (Pt), a reference electrode comprising Pt, and a plurality of connectors coupled to the plurality of potentiometric sensors to connect the plurality of potentiometric sensors in series.

20 Claims, 13 Drawing Sheets

(56) References Cited

U.S. PATENT DOCUMENTS

| | | | |
|---|---|---|---|
| 2003/0121780 A1* | 7/2003 | Dutta | C04B 35/486 204/424 |
| 2004/0074285 A1 | 4/2004 | Dimeo, Jr. et al. | |
| 2005/0016848 A1* | 1/2005 | Sahimi | G01N 27/4071 204/427 |
| 2005/0051511 A1 | 3/2005 | Ke et al. | |
| 2005/0214170 A1 | 9/2005 | Kading | |
| 2007/0114130 A1 | 5/2007 | Lankheet et al. | |
| 2007/0289870 A1* | 12/2007 | Nair | G01N 27/4062 204/424 |
| 2009/0026076 A1 | 1/2009 | Yang | |
| 2009/0065370 A1* | 3/2009 | Nair | G01N 33/0054 205/781 |
| 2010/0264900 A1 | 10/2010 | Blackburn et al. | |
| 2012/0247186 A1* | 10/2012 | Sanjeeb | G01N 33/0037 73/31.05 |
| 2013/0075255 A1 | 3/2013 | Moon et al. | |

OTHER PUBLICATIONS

Hunter et al., "Smart Sensor Systems for Human Health Breath Monitoring Applications," Journal of Breath Research, 2011, vol. 5, pp. 1-11.

PCT International Search Report and Written Opinion for PCT/US2014/027889, dated Jun. 30, 2014, pp. 1-17.

\* cited by examiner

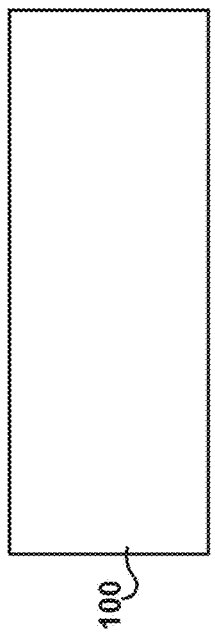
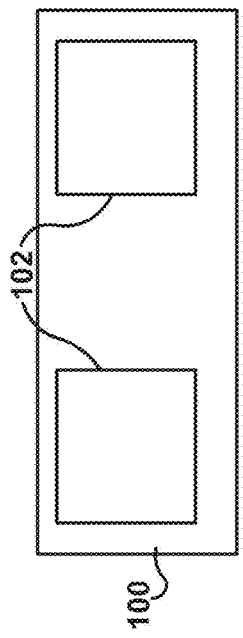
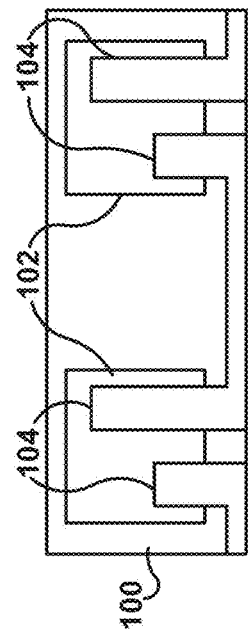
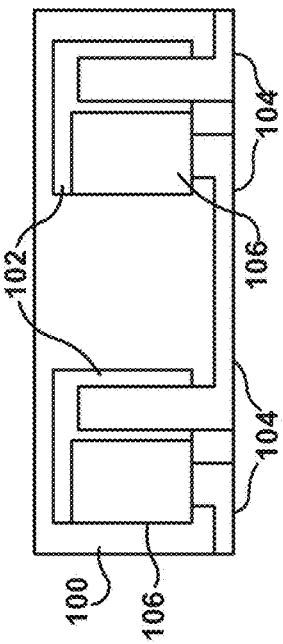
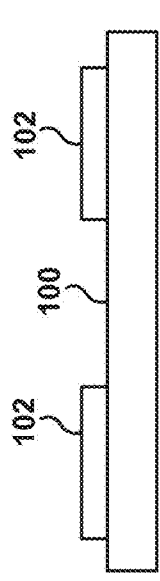
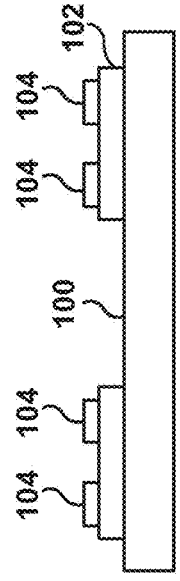
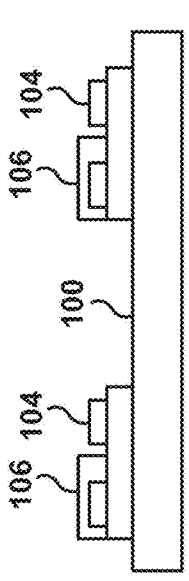

MINIATURIZED GAS SENSOR DEVICE AND METHOD

RELATED APPLICATION

This patent application is a continuation of U.S. application Ser. No. 15/693,266 filed Aug. 31, 2017, which is a divisional of U.S. application Ser. No. 14/212,006 filed Mar. 14, 2014, which claims the benefit of U.S. Provisional Application No. 61/801,106 filed on Mar. 15, 2013, the entirety of which is incorporated by reference herein.

TECHNICAL FIELD

The embodiments of the present invention relate generally to gas sensors. More specifically, the disclosure relates to miniaturized gas sensors that detect $NO_x$ gas.

BACKGROUND OF THE INVENTION

Nitric oxide (NO) sensing is a critical capability for a variety of applications ranging from high temperature combustion to clinical analysis. In high temperature combustion applications, detection of nitrogen oxides ($NO_x$) is critical in controlling the processes used to reduce the $NO_x$ emissions produced by the leaner combustion processes being developed to improve fuel efficiency. $NO_x$ sensors that are high temperature capable may also find use in other high-temperature applications. Another area where $NO_x$ sensing is required is in the medical industry, specifically in breath analysis. These do not typically involve applications where the sensor operates in a high temperature ambient environment, but it is one where the detection of nitric oxide (NO) itself has high importance.

There are a variety of ways to detect NO, with solid-state electrochemical sensors being one such technique. Such sensors also have the added benefit of being easier to miniaturize compared to other techniques. A variety of solid-state electrochemical sensors for NO have been demonstrated previously. These techniques vary and a continuing challenge is to design sensitive systems with limited size, weight and power consumption so as to allow for portable sensor systems. Such advancements would have notable impact on the healthcare industry in enabling home-care monitoring units.

NO sensors capable of detecting NO at concentrations as low as 7 ppb have been demonstrated using an array of sensor units in series to increase the resulting sensor signal for a given NO concentration. However, these sensors were made using hand assembly techniques and also were assembled into arrays by hand. This manual fabrication limits the minimum size to which the sensors can be reduced.

Miniaturized sensors based on microelectromechanical systems (MEMS) fabrication technology have been demonstrated for aerospace applications. Sensors made by MEMS fabrication are very small devices that can be made up of components and features between 1 to 100 micrometers in size (0.001 to 0.1 mm). Fabrication is a challenge at these size scales for several reasons. Large surface area to volume ratio of MEMS, and the resulting surface effects which dominate over volume effects can improve sensor performance. However, the overall surface area of a MEMS sensor unit may be notably smaller than corresponding macro sensor devices. This may decrease the overall number of chemical reactions involved, resulting in a decreased signal. Thus, improved sensor design is mandatory to enable miniaturization of sensor systems. Such optimization may be different on the macro level then for micro sensors, and simple application of design principle that are successful for macro sensor can lead to significantly degraded performance for micro sensors.

A reduction in size of the sensors using MEMS techniques would not only decrease the size for better implementation in a handheld home monitoring unit, but the reduced size would also decrease the power required to bring the sensors up to operating temperature. In addition, the utilization of MEMS fabrication techniques introduces batch fabrication that allows for multiple sensors to be made at one time, thus reducing costs.

SUMMARY

Various embodiments of a microfabricated gas sensor device and method of fabricating a miniaturized gas sensor device are provided. In one embodiment a microfabricated gas sensor device includes a base substrate, an electrolyte layer disposed on the base substrate and a plurality of potentiometric sensor units electrically coupled together on the base substrate. Each potentiometric sensor unit includes an electrolyte layer disposed on the base substrate, a sensing electrode comprising tungsten oxide ($WO_3$), a reference electrode comprising platinum (Pt), and a plurality of connectors coupled to the plurality of potentiometric sensors to connect the plurality of potentiometric sensors in series. The structure of each of these potentiometric sensor units is designed to greatly improve sensor response.

BRIEF DESCRIPTION OF THE DRAWINGS

The example embodiments of the present invention can be understood with reference to the following drawings. The components in the drawings are not necessarily to scale. Also, in the drawings, like reference numerals designate corresponding parts throughout the several views.

FIGS. 3*a*-3*b* illustrate an alumina substrate used for sensor fabrication;

FIGS. 4*a*-4*b* illustrate the deposition of YSZ islands during sensor fabrication;

FIGS. 5*a*-5*b* illustrate the deposition of the Pt electrodes during sensor fabrication;

FIGS. 6*a*-6*b* illustrate the deposition of $WO_3$ during sensor fabrication;

DETAILED DESCRIPTION

The various embodiments of miniature NO sensors disclosed herein is an electrochemical sensor whose structure includes sensor units of solid electrolyte, a reference electrode and a working electrode. An electromotive force (EMF) is induced between the working and reference electrodes when NO impinges on the sensor due to the dissimilar chemical activity at each electrode. In one embodiment, the reference electrode is platinum (Pt), while the sensing or working electrode is tungsten oxide ($WO_3$). The solid electrolyte is yttria-stabilized zirconia (YSZ). These sensor material choices are based on larger hand-made sensors that are described further in the examples below.

Figure 1:
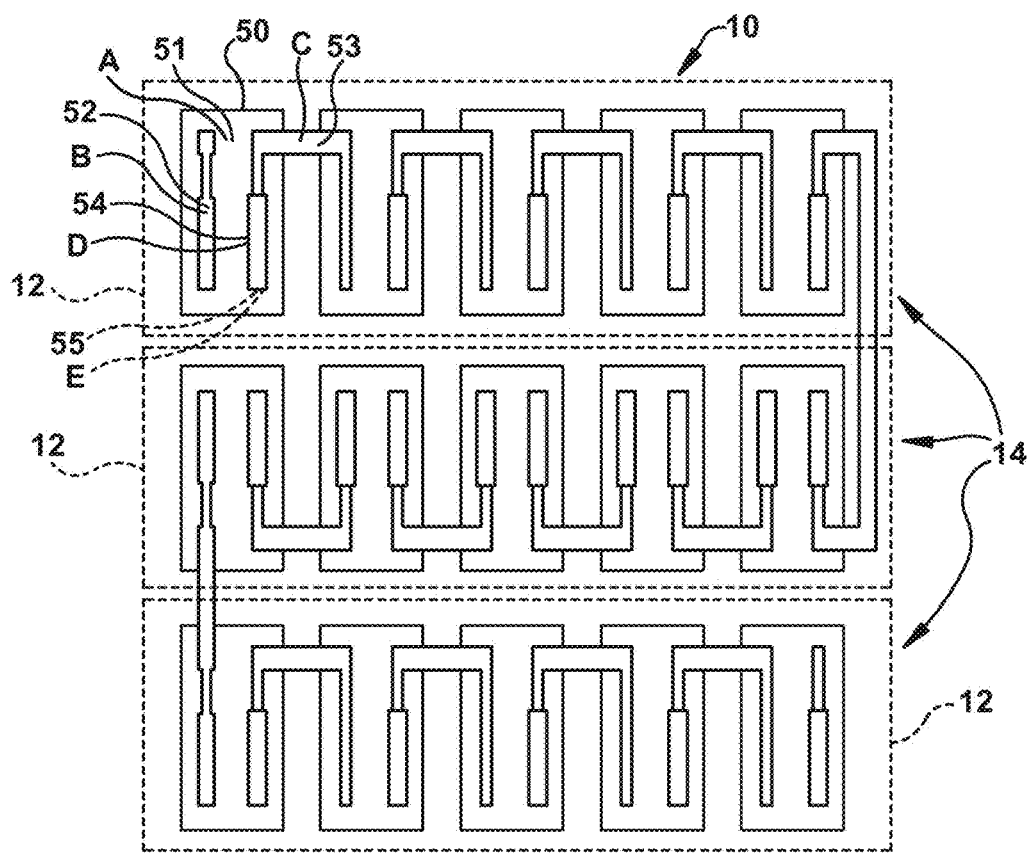
FIG. 1 illustrates a miniature sensor device, which is a first generation design using shadow masks, according to an embodiment of the present invention.

FIG. 1 shows a miniature sensor device 10 having individual sensor units 50 and fabricated on aluminum oxide substrates 12. Each sensor on the substrate comprises a YSZ island 50 upon which the rest of the sensor is built. Pt reference electrode 52 and $WO_3$ sensing or working electrode 54 lie on top of the YSZ island 51. A Pt contact 55 of the sensing electrode is located below the $WO_3$ to make contact to the $WO_3$ of this two-part sensing or working electrode. As each sensor 50 is an electrochemical cell, the sensors can be connected in series to generate a larger signal response. Thus, an array of sensors can be used to improve the signal response to NOx, including NO. The sensors are electrically connected together as in the cells of a battery such that the induced EMF's are additive, thereby increasing the response for a given NOx concentration over a single sensor. Sensor devices of 5, 10, 15 and 20 sensors were connected electrically and tested. Each sensor array is interconnected electrically via Pt leads. This fabrication approach represents a simple reduction in size of the larger in the sensors and it has been found herein, as demonstrated in the examples below, that simple reduction in size does not result in the desired sensitivity needed to improve sensor performance.

With reference to FIG. 1, the gas sensor device 10 includes a plurality of, i.e. or at least two, sensor units 50 in a dice unit row 12. Each of the sensor units 50 includes a reference electrode 52 and a sensing electrode 54. In one embodiment, the sensing electrodes 54 comprise $WO_3$, and the reference electrodes 52 comprise platinum (Pt).

In one embodiment, the gas sensor device 10 includes 3 rows 14 of sensor units 14, but a variety of sensor units 50 is possible. Each of the sensor units 50 is electrically coupled to at least one adjacent sensor unit 50. For example, the sensor units 50 are electrically connected together in series. The combined potential difference of the plurality of sensor units 50 is approximately a sum of the potential differences of each of the individual sensor units 50 electrically connected to one another.

Experimental tests that have been conducted herein show that the sensitivity of the system 10 is based on the number of sensor units 50. Each of the sensor units generates a potential difference in the response to a gas, for example, $NO_x$ gas. Generally, a system including more sensor units 50 has been found to be relatively more sensitive to NO, and a system including less sensor units has been found to be relatively less sensitive to NO. However, there is a point at which additional sensor units 50 will not improve the sensitivity, and it has been found that sensor devices that have 15-20 sensor units have increased sensitivity. This is due to lack of previous recognition of the various elements of sensor design including, for example, the internal resistance of each sensor element. As noted above, a corresponding reduction of the size of the sensor having the same materials of construction do not result in improved sensitivity. The impact of the internal resistance of the individual sensor units, and the design features that contributed to higher sensitivity is described herein and was discovered during the course of the fabrication of sensors as discussed in the examples below. Overcoming internal resistance is core to even higher levels of sensitivity.

Figure 2:
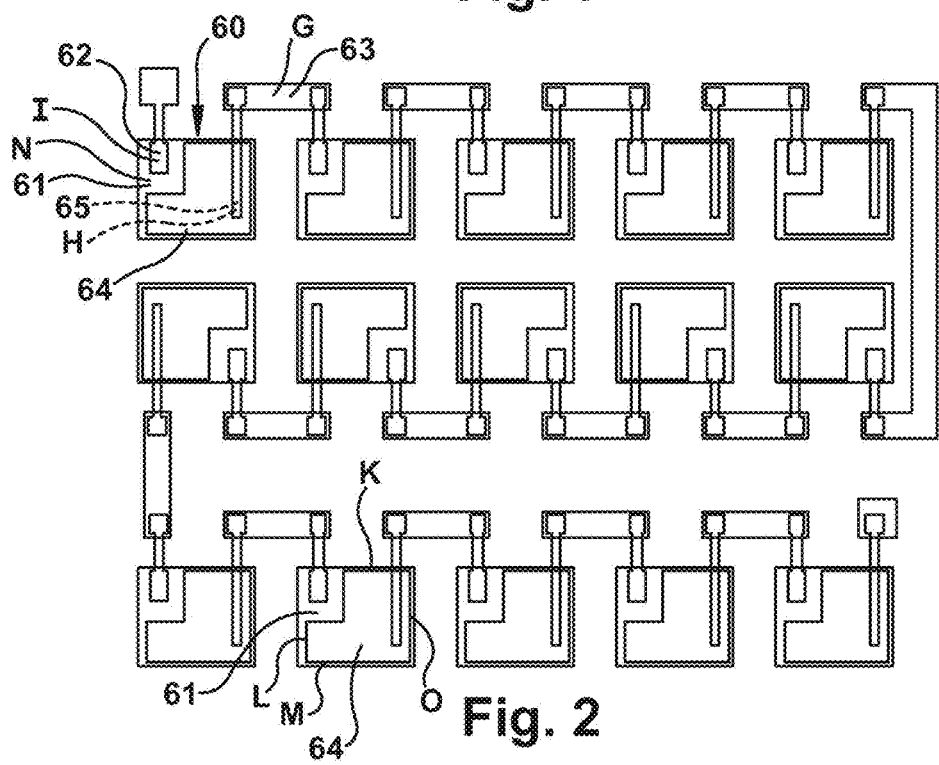
FIG. 2 illustrates a miniature sensor device, which is a second generation design using shadow mask, according to an embodiment of the present invention.

It has been found herein, in accordance with various embodiments of the present invention, that reducing the exposed surface area of Pt reference electrode on the YSZ electrolyte and increasing the surface area of $WO_3$ electrode covering the YSZ electrolyte improves the sensitivity of the sensor as can be seen in comparing the results of the first generation, shadow mask design of FIG. 1 and second generation, shadow mask design of FIG. 2 and shown in the results of the examples. FIG. 2 shows a miniature sensor device having individual sensor units 60 and fabricated on a substrate, for example, aluminum oxide substrates. Each sensor on the substrate comprises a YSZ island 50 upon which the rest of the sensor is built. Pt reference electrode 62 and $WO_3$ sensing or working electrode 64 lie on top of the YSZ island 61. A Pt contact 65 of the sensing electrode is located below the $WO_3$ to make contact to the $WO_3$ of this two-part sensing or working electrode. As each sensor unit 60 is an electrochemical cell, the sensors can be connected in series as a sensor device to generate a larger signal response. Thus, an array of sensors can be used to improve the signal response to NO.

The ratio of the exposed $WO_3$ to the exposed platinum Pt is maximized to increase the sensitivity and obtain a low end sensor reading. Furthermore, in another embodiment, the ratio of the exposed $WO_3$ to the exposed platinum Pt is maximized while also decreasing the size, for example the surface area, of the Pt contact of the sensing electrode that is contact with $WO_3$. Decreasing the size of the contact 65 underneath the $WO_3$ so that it is minimized to the extent of fabrication (i.e. within the resolution of the fabrication approach, such as 2 microns) is found to increases the sensitivity of the microfabricated sensors units 60. This electrode structure is not a simple one component electrode, but rather composed of both an oxide and metallic electrode combination that together are designed for improved response. In accordance with an embodiment of the present invention, the electrolyte layer of the microfabriated potentiometric gas sensor device has a thickness of the electrolyte layer that is maximized a sufficient amount to minimize the internal resistance of the potentiometric sensor unit, and such that the internal resistance of each of the plurality of sensor units is minimized so as to minimize the overall resistance of the sensor device to increase the sensitivity of the sensor device.

For example, in one embodiment the surface area of the $WO_3$ electrode on the electrolyte is greater than the surface area of the Pt electrode. In another embodiment the $WO_3$ covers all of the available surface on the YSZ unused by the Pt electrode within the resolution of the fabrication approach (approximately 2 microns depending on the equipment used). In another embodiment the surface area of the $WO_3$ electrode is at least two times greater than the surface area of the Pt electrode, and in another embodiment, the $WO_3$ electrode is at least 5 times greater than the surface area of the Pt electrode, and in yet another embodiment the $WO_3$ electrode is at least 10 times greater than the surface area of the Pt electrode.

The increased surface area of the $WO_3$ boundaries does increase the triple point boundary of the $WO_3$ electrode, the YSZ electrolyte and the gas, for example, NO gas compared to those of the Pt electrode. The decreased surface area of the Pt electrode decreases the triple point boundary of the Pt, the YSZ electrolyte and the gas. The limitation on the amount of YSZ surface area that is not also a triple point boundary is believed to decrease the sensitivity of the sensor. As a result it has been found that the sensitivity of the sensor device can be increased.

Figure 9:
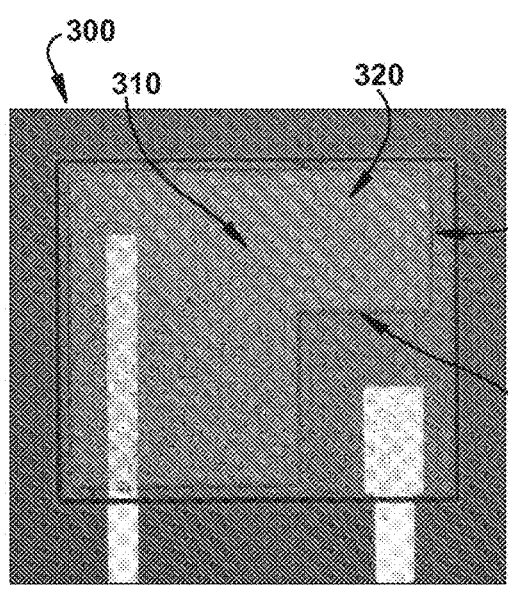
FIG. 9 illustrates aphotographic image taken under a microscope of a sensor unit of the second generation, shadow mask design of FIG. 2, according to an embodiment of the present invention.
Figure 10:
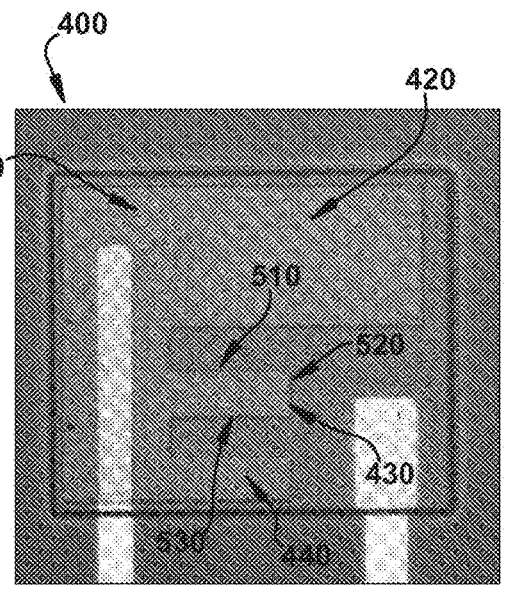
FIG. 10 illustrates a photographic image taken under a microscope of an alternative miniature sensor unit of a second generation, shadow mask design, according to an embodiment of the present invention.
Figure 11:
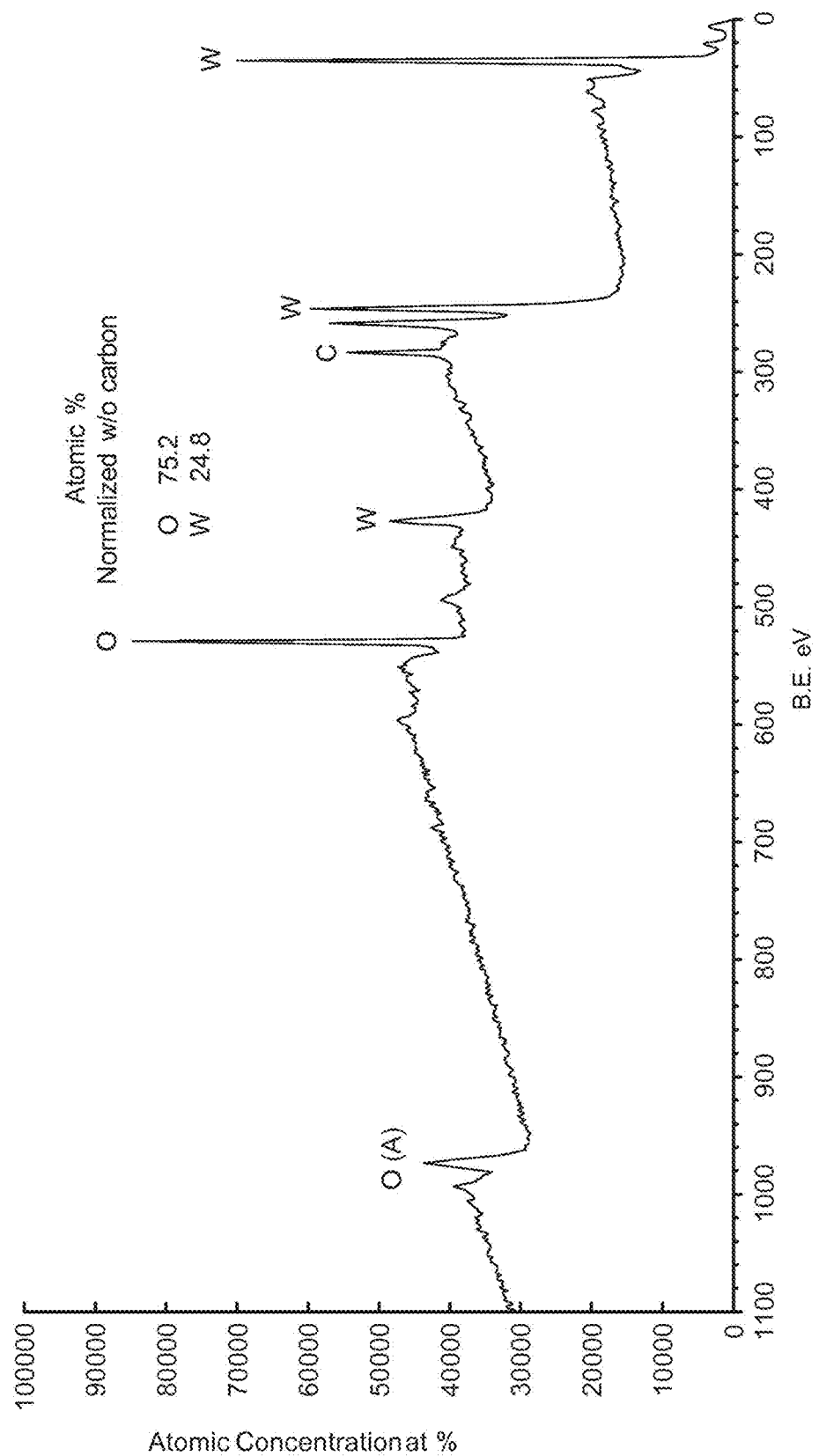
FIG. 11 illustrates the spectrum from XPS analysis of sputter deposited $WO_3$ film, in accordance with an embodiment of the present invention.

In addition FIG. 9 shows that the surface of the $WO_3$ electrode 310 of sensor unit 300 has at least one lateral projection 320. The at least one lateral projection has at least two edge interfaces 330, 340 along the surface of the electrolyte, and in another embodiment at least three edge interfaces, thereby creating additional triple point boundary points between the $WO_3$ electrode and YSZ electrolyte. In another embodiment, FIG. 10 shows that the surface of the $WO_3$ electrode has three lateral projections 420, 430 and 440. Each lateral projection has at least three edge interfaces 510, 520 and 530 along the surface of the electrolyte which forms a triple point boundary between the $WO_3$, the YSZ electrolyte and the gas. As shown the lateral projections form corners formed by the edge interfaces 520 and 530. These lateral projections increased the torturous nature of the pattern and increase the number of triple points. For example, these lateral surface contours increase the lineal length of edge interface between the $WO_3$, the electrolyte, and the surrounding gas as illustrated in FIGS. 9 and 10.

Further, the size of the YSZ patterns in FIG. 2 compared to FIG. 1 decreases the distance, and thus corresponding resistance, between the electrodes. Other factors decreasing this resistance include the thickness of the electroylyte, yttria-stabilized-zirconia, and thickness of the various metal layers that are micro-deposited on the surface. Such features are not apparent in macro sensor since, for example, a 5 micron change in the thickness of the zirconia in a macro sensor has much less effect on the internal resistance of the sensor unit where it would nearly eliminate the zirconia layer for a microfabricated sensor.

It should be noted that this is a potentiometric sensor (voltage difference), rather than an amperiometric sensor (current flow). In a sensor that measures current flow, the effect of resistance is known and too large a resistance can readily be seen to limit the measurement. Such amperometric sensors are not linked in series like batteries (as are the potentiometric sensors in our work) and the effect of increase resistance is directly noticeable in the measurement. It is discovered that an aspect of the potentiometric sensor device that includes sensor units linked in series, is that high resistance of each sensor unit was found to limit the lower detection limit of the sensor overall. Thus, while each sensor unit might have a resistance that did not notably affect its operation; the combined resistance of each of the potentiometric sensor unit in series can change the lower limit detection capabilities of the overall sensor. This may not be obvious at higher concentrations, but was found to have significant effect on sensitivity for lower concentration measurements. It was found that decreasing this overall resistance is a feature of increasing the sensor's lower detection limit.

The microfabricated potentiometric gas sensor device senses gas at a broad range of temperatures, including but not limited to, high temperatures that range from about 500° C. to about 700° C., in another embodiment, from about 550° C. to about 650° C.

Method of Fabrication

MEMS fabrication has been successfully implemented in the examples herein, where sensors are batch fabricated on a single wafer, with each wafer containing multiple sensors units. These examples show that applying the concepts above are not only achievable but improve the capability of the sensor. These examples are meant to show different aspects of the design optimization from large to smaller sensors and so while one example may show improved response time but decreased response, it is the combination of the various design features that is understood to provide an improved sensor system, or may be used as needed to emphasize certain aspects of the sensor response. The sensors are fabricated using masks and thin film deposition techniques. Each layer of the structure is deposited via sputtering from a target containing the desired material or a component of the desired material, with the masks serving to define the shape of the resulting deposited film. The fabrication of these sensors was carried out using thin metal, shadow masks or photoresist masks. The sensors were fabricated on two-inch alumina wafers.

Figure 7:
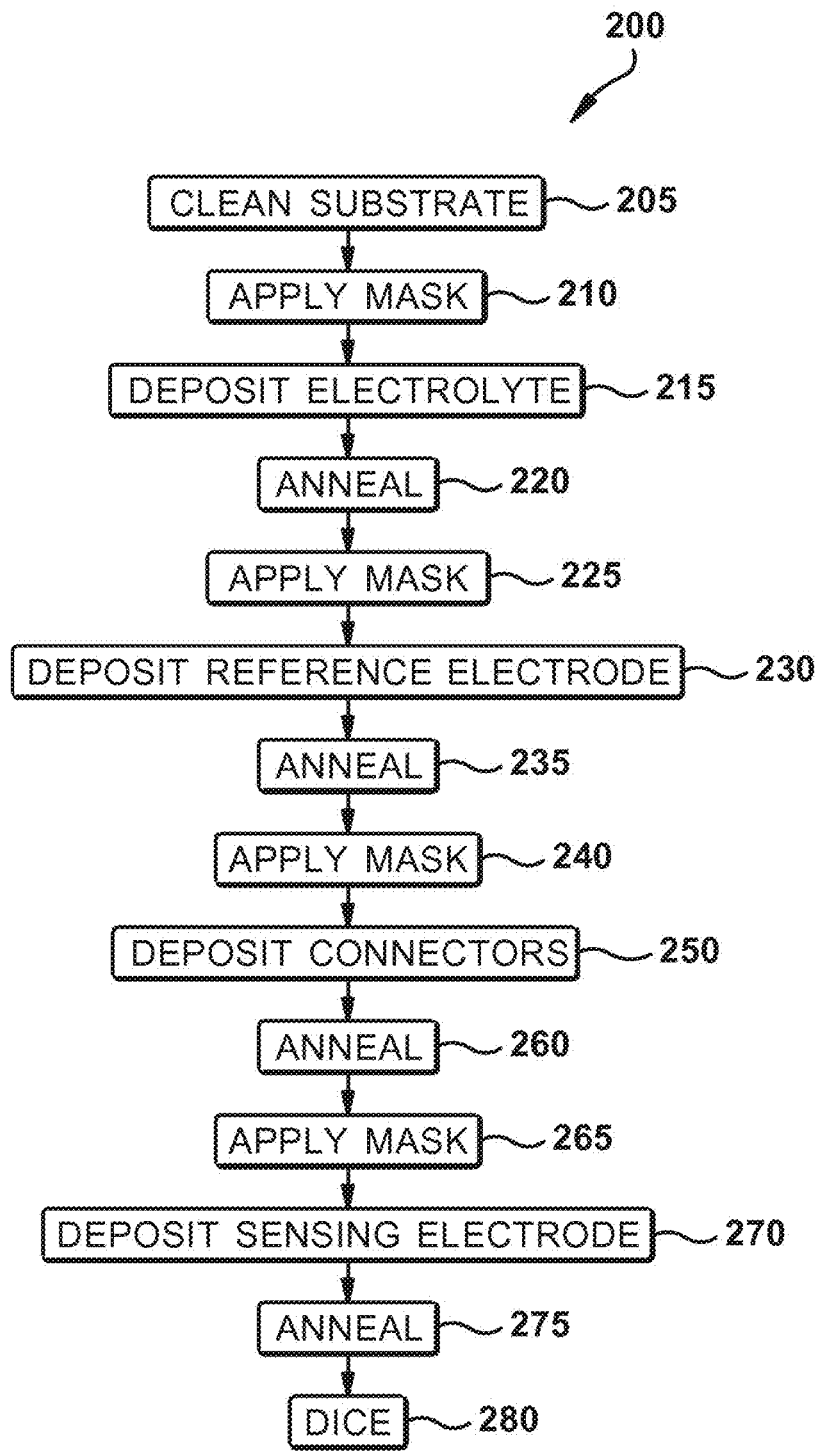
FIG. 7 is a flow chart of the method for making the sensor device, according to an embodiment of the present invention.

The general process flow for the sensors is shown in FIG. 7. The first step in the fabrication process is to clean the alumina wafer using a combination of solvents, generally acetone followed by isopropanol. The YSZ islands are sputter deposited using the first mask, forming individual rectangular islands of YSZ. A thermal anneal is then carried out at 1000° C. for two hours in air ambient to densify the YSZ. The Pt electrodes are then deposited using the next mask. A second platinum layer is sputter deposited to form the interconnects, electrically connecting the sensors in the array. It should be noted that in some designs of the sensor device the Pt interconnects are deposited at the same time as the first Pt electrode deposition. Finally, the $WO_3$ is reactively sputter deposited from a tungsten target in an argon/oxygen atmosphere using the third mask. The sensors are then diced into individual arrays following the final film deposition.

The three films that are deposited are the YSZ, Pt, and $WO_3$ films. Both the YSZ and Pt films are deposited by a sputter deposition process. The WO3 also is deposited by a sputter process. However, the sputter process is a reactive sputter process using a tungsten (W) target whereby a W target is sputtered to produce W atoms that are then reacted with an oxygen gas flow in the chamber prior to impingement on the substrate where they are deposited as $WO_3$. The deposition is done at room temperature using a cooled substrate to keep the substrate cool. XPS analysis on the films confirmed the proper stoichiometry of the films after the sputter deposition processes, as shown in FIG. 10. No sensors fabricated using thin film microfabrication techniques that are significantly smaller than such sensors are herein demonstrated. Changes made from the initial design to the size of both the reference and working electrode as well as the contacting Pt electrode under the working electrode resulted in improved sensitivity of the sensor. These sensors have demonstrated sensitivity below the ppm level.

FIGS. 3 through 6 illustrate a sensor array at various steps of a fabrication process, according to an embodiment of the present invention. Cross-sectional and top views are shown left and right, respectively: (a) Alumina substrate, (b) deposition of YSZ islands, (c) following deposition of Pt electrodes, (d) sensor after deposition of $WO_3$, according to an embodiment of the present invention;

FIGS. 3A and 3B show the base layer of alumina used in the substrate 100 in an embodiment of the present invention. FIGS. 4A and 4B show a side view and top view, respectively, of the alumina substrate 100 with an electrolyte layer 102 deposited on the substrate. FIGS. 5A and 5B show a side view and top view, respectively, of the substrate 100 with the electrodes 104 deposited on top of the electrolyte layer 102. FIGS. 6A and 6B show the side view and top view of the tungsten oxide $WO_3$ electrode 106 which is the working electrode deposited on top of the Pt contact 104.

FIG. 7 illustrates the process step for making the gas sensor. In one embodiment the box 205 shows the first step of cleaning the alumina wafer substrate. Solvents or combinations of solvents, for example alcohols acetone and isopropanol, or an application of solvent in a series of acetone followed by isopropanol can be used to clean the substrate. In box 210 the mask is placed on the substrate, a thin metal mask for the shadow mask design and a photoresist mask in the photoresist design n box 210, for the photoresist design the photo resist mask is applied to the surface of the substrate. Once the photoresist mask is deposited, the substrate is soft baked to remove some of the solvents in the liquid photoresist. Then the photoresist is placed under a UV light source and the UV light is selectively passed through a glass mask with defined openings through which light may pass to the photoresist. Depending on whether the photo resist is positive or negative, the resulting regions exposed to light will either become more soluble or less soluble respectively after exposure to the UV light. The substrate is then placed into a developing solution that removes the more soluble regions of the photo resist. The substrate is then placed under heat for a hard bake of the photo resist mask. In the next step of box 215 the process includes depositing a layer of electrolyte using a sputter deposition of the desired film. The photo resist is then removed by a solvent, usually acetone, and the sputtered film on top of the photo resist is also removed leaving behind the thin film that was defined by the openings in the photo resist mask. The photo resist mask has precisely defined features down to below 100 micrometers which is a much smaller resolution than the shadow mask used in the embodiments described above. Next in box 220 the substrates were annealed in the presence of oxygen in order to remove or clean the residual photo resist from the surface. It was found that standard techniques to remove the photo resist perform poorly and the miniaturization process did not provide good results compared to the shadow mask method of making the sensor when using the standard software-based photoresist removal techniques. The oxygen annealing temperature to remove the residual photo resist on the surface or in the pores of the films of the sensor can be carried out at a temperature that is at least 350° C., and another embodiment from about 350° C. to about 450° C., and in another embodiment from about 390° C. to 425° C. It has been found that residual photoresist can notably affect sensor response and the oxygen annealing step, in accordance to an embodiment of the present invention was found to improve sensitivity.

Still referring to FIG. 7, the process for making the gas sensor further includes applying another mask over the electrolyte layers and next in box 230 the process further includes depositing the reference electrode material and contact material for the sense electrode over the mask but through sputtering. The mask is removed and for the photoresist-based sensor the substrate is again annealed to remove residual mask material in box 235. Next in box 240 another mask is again applied over the substrate and over the electrodes to deposit the connectors in box 250. In another embodiment the reference electrode, contact for the sense electrode, and the connectors can be applied in a single step after application of the mask in box 210. Next in box 260 the mask is removed and for the photoresist-based sensor the substrate then undergoes the annealing process to remove the residual photoresist. Next in box 265 the mask is applied again and then in box 270 the sensing electrode is deposited by reactive sputtering. Next the mask is removed and for the photoresist-based sensor the substrate undergoes another annealing process as shown in box 270 to remove all residual photoresist. Finally, in box 280 the substrate can undergo dicing to separate the individual sensor arrays 10 on the substrate. The oxygen annealing temperatures of boxes 235, 260, and 275 are carried out and are the same as the temperature ranges described above with respect to box 220.

The results of the testing on these various generations of designs indicate that the changes that were made between each generation were indeed beneficial to the overall performance of the sensor. Reducing the exposed Pt on the YSZ and increasing the WO3 covering the YSZ improved the sensitivity of the sensor as can be seen in comparing the results of the first and second generation shadow mask designs. The resulting design changes were applied to the photomask-based design, which is basically the second generation shadow mask design reduced in size by a factor of 0.35. The test results of the photoresist design indicate that the sensor array should be capable of sensing down to at least 500 ppb level, and in another embodiment down to about 300 ppb level.

In another embodiment, the several embodiments of the NO sensor device described above can be used in an apparatus for measuring the level of NO. The apparatus includes the sensor device and an inlet for receiving a gas sample. The gas sample, for example, NO gas, is in fluid communication with the sensor. The potential difference is indicative of a level of NO within the original sample. In one embodiment, the gas sample is a breath sample from the subject. In another embodiment, the gas sample that enters the apparatus may be treated by humidification or dehumidification to improve the sensitivity. The potential difference of the sensor array 10 is a summation of the individual potential differences across the individual sensor units in response to presence of the NO in the gas sample.

EXAMPLES

Examples—Shadow Mask Fabrication

The shadow mask version of the sensor arrays utilized a metal shadow mask during each of the deposition processes to define the deposited films into the desired features. The metal masks were placed onto the substrate and clamped at the edges of the substrate. The shadow masks are easy to use and are aligned from one mask layer to the next. However, the defined features are rather large in size, there can be distortion in the shadow mask resulting in edges of the defined shapes that are not sharp, and after multiple uses the resulting film build up on the shadow masks may cause warpage of the shadow mask and/or micromasking during the deposition process as particles fall off of the shadow mask and land on the openings defined by the mask.

For comparison, our initial sensor design is shown in FIG. 1 with corresponding dimensions, along with the second generation, shadow mass that is illustrated in FIG. 2. FIG. 1 shows that the electrolyte island 51 dimension A is 1.55 mm by 2.88 mm; the Pt reference electrode 52 of dimension B is 1 mm×0.21 mm; the Pt interconnect 53 of dimension C has an outer length of 1.56 mm and an inner length of 1.15 mm; the sensing electrode 54 of $WO_3$ has a dimension D of 1.1 mm×0.31 mm; and the Pt contact 55 of the sensing electrode E is approximately the same surface area as the reference electrode 52. FIG. 2 shows that the electrolyte island 61 dimension N is 1.328 mm by 1.55 mm; the Pt reference electrode 62 of dimension I is 0.4 mm×0.21 mm; the Pt interconnect 63 of dimension G has dimensions of 0.33 mm×1.4 mm; the $WO_3$ of sensing electrode 54 has an "L" shape that can be calculated by dimensions L (0.54 mm), M (1.4 mm), O (1.22), and K (0.88); and the Pt contact 65 of the sensing electrode has dimensions H, 1.5 mm×0.1 mm.

Figure 12:
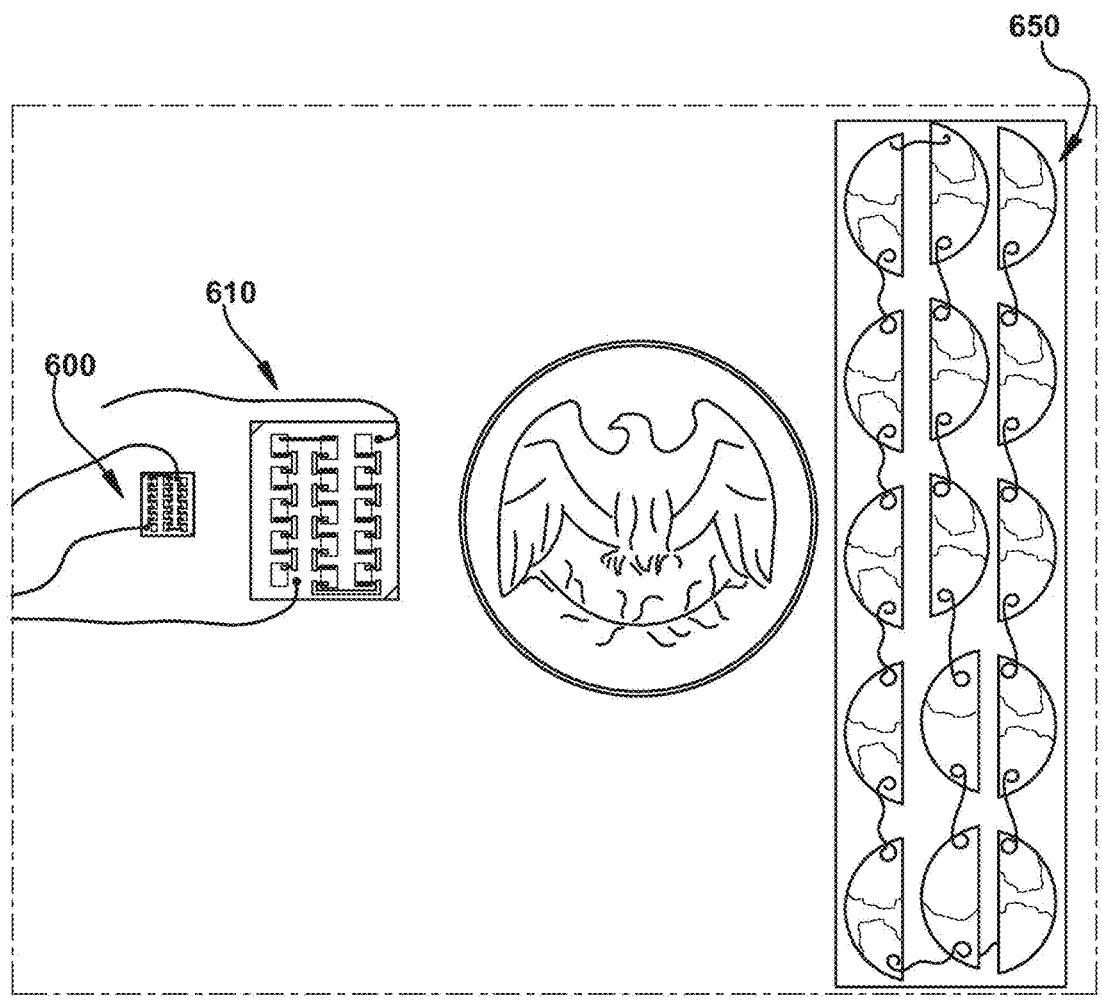
FIG. 12 illustrates a miniature sensors of the second generation shadow mask design, and a photoresist version of the miniature sensor compared to a hand fabricated sensor, according to an embodiment of the present invention.

FIG. 12 illustrates a comparison of sensors to hand fabricated sensor on the far right, with a quarter shown for size reference. The shadow mask version of the sensor is to the left of the quarter and is 10 mm by 12 mm. The photoresist version of the sensor is to the far left and is 3 mm by 4 mm in size.

In comparing the first and second generation shadow mask designs, the size of the $WO_3$ covering the YSZ is increased by a factor of 4.0 from 0.341 $mm^2$ to 1.35 $mm^2$ for the $WO_3$ on the YSZ in moving from design generation one to two. Similarly the Pt reference electrode was decreased in size by a factor of 2.5 from 0.21 $mm^2$ to 0.084 $mm^2$ in moving from design generation one to two. The size of the YSZ island for each individual sensor is 1.55 by 2.28 $mm^2$ for generation one and 1.328 by 1.55 $mm^2$ for generation two designs. These designs are shown in FIGS. 1 and 2.

Examples—Photoresist Process

The second variation of the sensors that was fabricated was a photoresist-based version of the sensors. In this version of the sensor arrays, the deposited films are defined by photoresist layers deposited on the substrate. In the photoresist process a liquid photoresist film is spun onto the surface of the substrate. Once the photoresist is soft baked to remove some of the solvents in the liquid photoresist, the substrate is placed under a UV light source that is defined by a glass mask. A thin metal film on the glass mask defines openings through which light may pass to the substrate. Depending on whether the photoresist is positive or negative, the resulting regions exposed to light will either become more soluble or less soluble, respectively, after exposure to the UV light. The substrate is then placed into a developer solution that removes the more soluble regions of the photoresist. After a hard bake the photoresist mask is ready to be used as the mask for sputter deposition of the desired film. Once the sputter deposition process is finished the sputtered film is defined by a lift-off process whereby the photoresist is removed by a solvent, usually acetone, and the sputtered film on top of the photoresist is also removed leaving behind the thin film that was defined by the openings in the photoresist mask.

The advantage of the photoresist mask versus the shadow mask is that the photoresist mask can define features to a much smaller resolution (e.g., down to about 2 micrometers). The photoresist version of the sensor was decreased to 0.35 times the size of the second generation shadow mask version, the sensors are otherwise identical in layout design. The downside to the photoresist mask is the possible contamination of the underlying materials with photoresist if they are porous. If the photoresist is not completely removed following the thin film deposition the resulting remnants may react at higher temperatures and form a barrier to gas reaction at the surfaces of the sensor. In fact, sensors that were initially fabricated using standard photoresist development and removal techniques performed poorly compared to the shadow mask versions. This link between photoresist contamination and degraded sensor performance was confirmed when shadow mask versions of the sensors that were covered with photoresist prior to dicing into individual arrays by the dicing saw were found to perform poorly compared to similar shadow mask sensors not subjected photoresist coating that were partially diced (pre-scribed) prior to fabrication. Several methodologies were attempted in removing any residual photoresist from the sensor surfaces. Continued solution in acetone and application of ultrasonic in acetone solution were both tried with little change in results. A typical solution to such a problem is to use an oxygen plasma clean to remove such residual photoresist. However, due to the nature of the films that were depositing, there was a small percentage of Na in the resulting films that precluded the employment of this oxygen plasma system as this was designated a MOS piece of equipment that should be free of exposure to salt containing films. Surprisingly, it was discovered that when the sample substrates were exposed to an oxygen annealing in a tube furnace after each photoresist step, residual photoresist was removed. This higher temperature process of about 400° C. removed the residual resist on the surface or in the pores of the films on the sensors. Sensors fabricated using this method produced the same or better results compared to equivalent shadow mask sensor arrays validating the employment of oxygen anneal to remove residual photoresist.

FIG. 12 is an optical image comparing arrays of sensors from hand fabricated down to photoresist based sensors. Each successive version of the sensor array is smaller in size, moving from the original hand built sensor array to the shadow mask version to the final photoresist-based version. As can be seen in FIG. 12, the photoresist sensor is over a magnitude smaller in each dimension compared to the hand fabricated version. The reduction in size allows for smaller heater stages to be used to heat the sensor and thus reduced power requirements.

Sensor Performance—Shadow Mask

Sensors were tested at temperatures ranging from 500 to 600 degrees Celsius to determine the efficacy of the sensors. Generally sensors were found to work best when operated between 550 and 600 degrees Celsius. The sensors were tested by bringing the sensors to temperature and awaiting the sensor's stabilization. Once the temperature was stable, various NO gas concentrations were introduced to the sensor. Air was generally used as the baseline gas for these experiments. In general, the electrical connections to the sensors were made via either probe tips or wires attached to the contact pads at either end of the sensor array.

Figure 8:
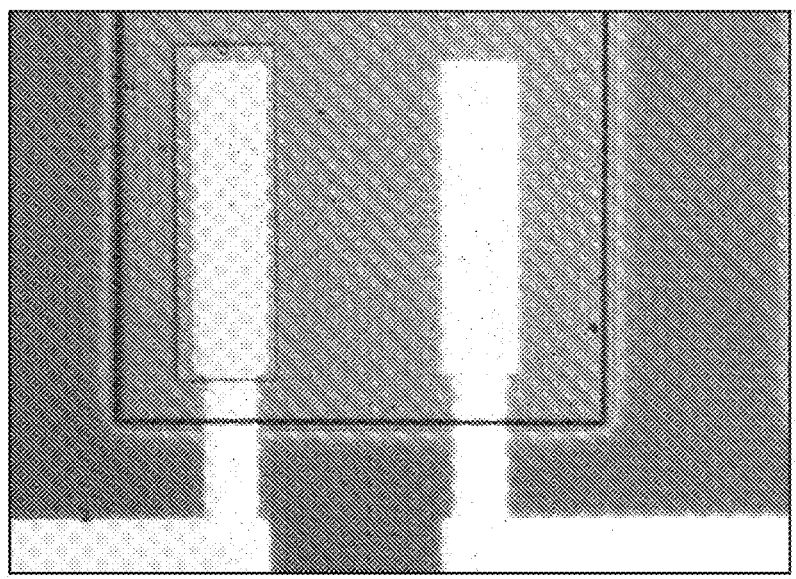
FIG. 8 illustrates a photographic image taken under a microscope of one of the sensor units in the first generation, shadow mask design of FIG. 1, according to an embodiment of the present invention.
Figure 13:
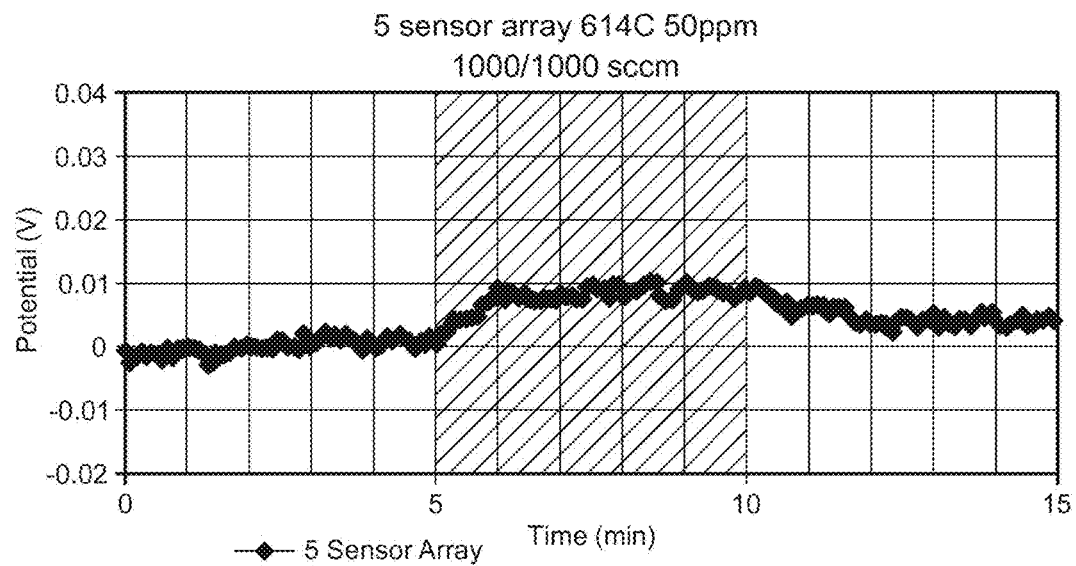
FIG. 13 illustrates the test results of a miniature five sensor unit device of the first generation, shadow mask sensor designat 50 ppm exposure to NO, according to an embodiment of the present invention.
Figure 14:
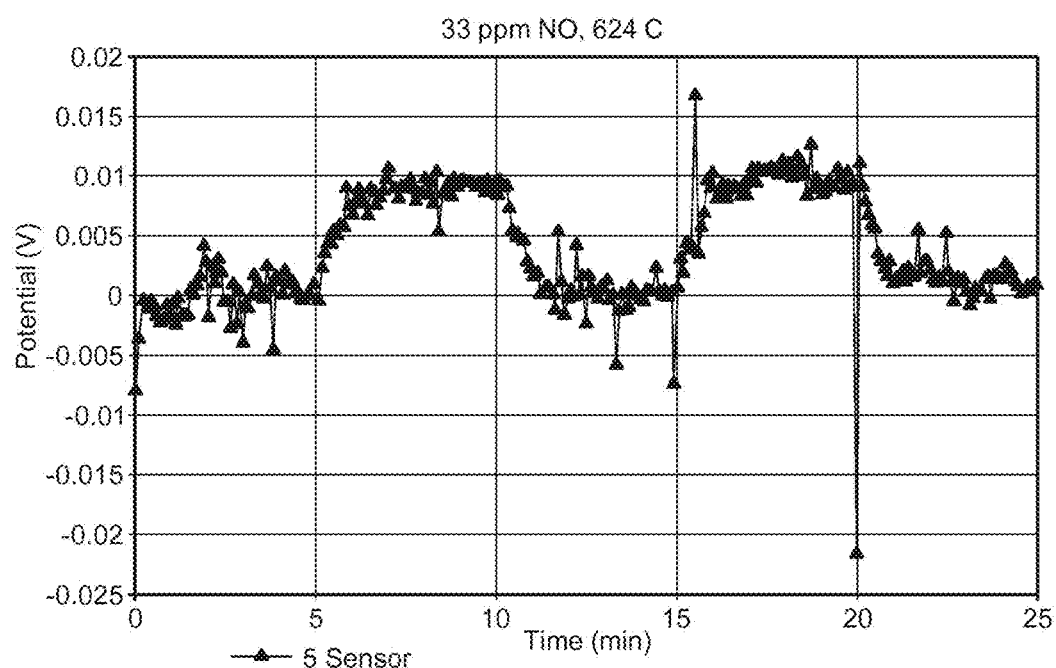
FIG. 14 illustrates the test results of a miniature five sensor unit device of a second generation, shadow mask sensor design at 33 ppm exposure to NO, according to an embodiment of the present invention.
Figure 15:
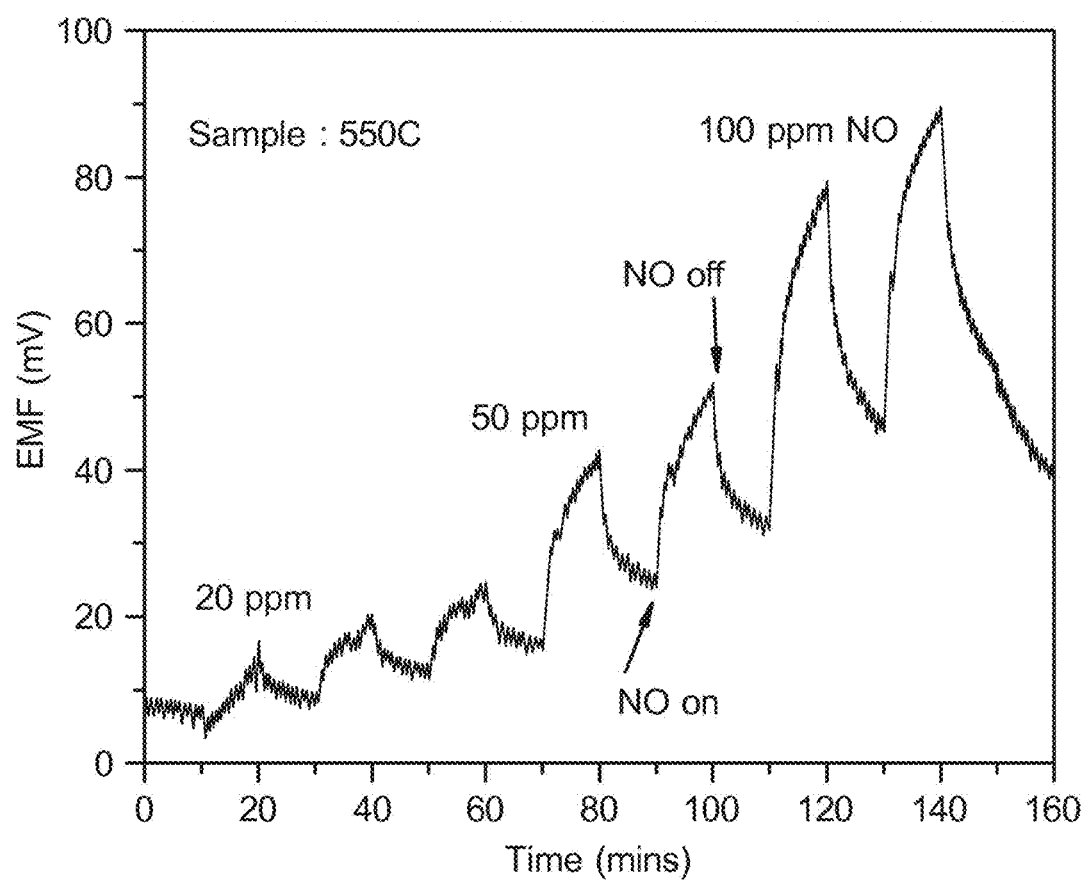
FIG. 15 illustrates test results of a miniature ten sensor unit device of a second generation, shadow mask design in a plot of sensor voltage response to 20 ppm, 50 ppm, and 100 ppm NO exposure, according to an embodiment of the present invention.

Test results of the initial first generation design are shown in FIG. 13. The tested sensor was a five sensor array. As can be seen from the results, the sensor response at 50 ppm was less than 10 mV for this concentration of NO. A photographic image of one of the sensors in this array is shown in FIG. 8. For comparison in FIG. 14, the results of testing on a second generation shadow mask design are shown for a five sensor array. This second generation five sensor array shows a response of nearly 10 mV for a 33 ppm concentration of NO. It can be deduced from these measurements that the sensor response increased quite significantly (showing an equivalent response for a concentration reduction of 1.5 times) due to the changes made from the first to the second generation shadow mask design. Also shown in FIGS. 9&10 are photographic images of two sensors, showing the two different designs of the sensor in the second generation design. FIG. 15 shows the results of testing with a 10 sensor array from this same wafer. The results are shown for the sensor tested at 550 degrees Celsius.

In addition it was found that sensor response of each individual sensor in the array could be maximized by applying and/or modifying several parameters. For the working electrode minimizing the Pt exposed on the YSZ and maximizing $WO_3$ film exposure were found to increase the sensor response for a given NO concentration. Pt exposure on YSZ was minimized at both the reference and working electrodes. This change was done to minimize the triple point boundaries between the gas, Pt, and YSZ and thus the reactions at the exposed Pt surfaces on YSZ, thereby decreasing competing reactions that would decrease the induced potential across the sensor. Similarly, it was found that maximizing the $WO_3$ film on top of the YSZ was found to increase the induced potential across the sensor. In this case, this was due to an increase in the number of triple-point boundaries between the gas, $WO_3$, and YSZ.

Sensor Performance—Photoresist

Figure 16:
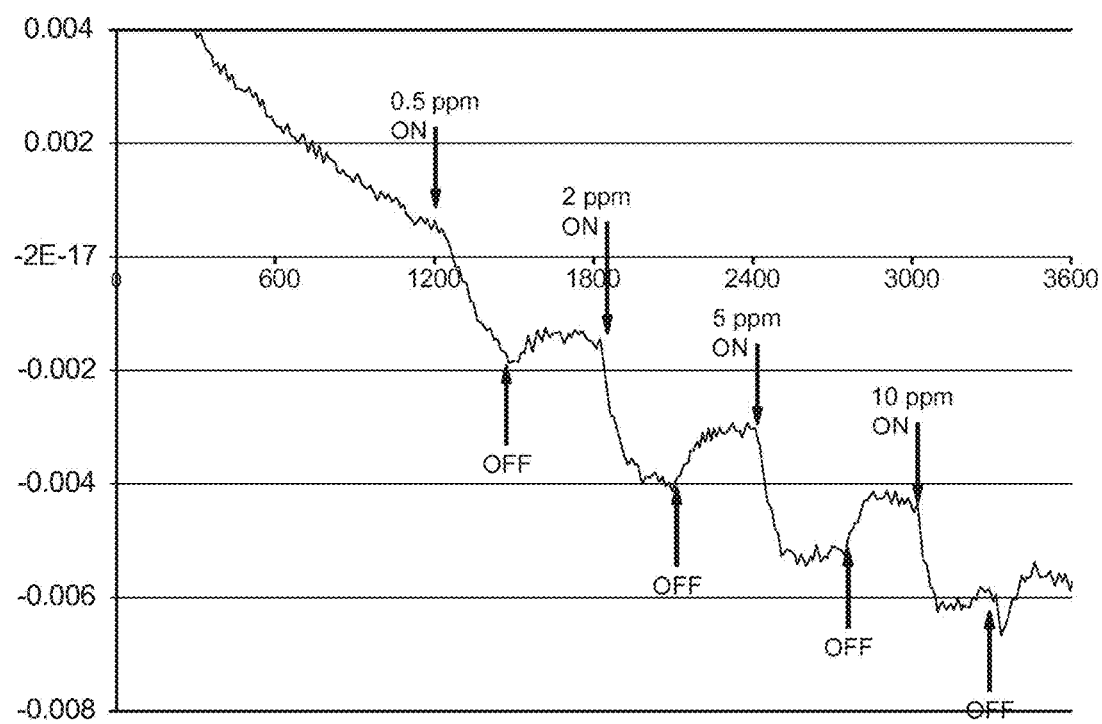
FIG. 16 illustrates the test results of a miniature fifteen sensor unit device of a second generation, photolithographic design in a plot of sensor response to 0.5 ppm, 2 ppm, 5 ppm, and 10 ppm NO exposure, according to an embodiment of the present invention.
Figure 17:
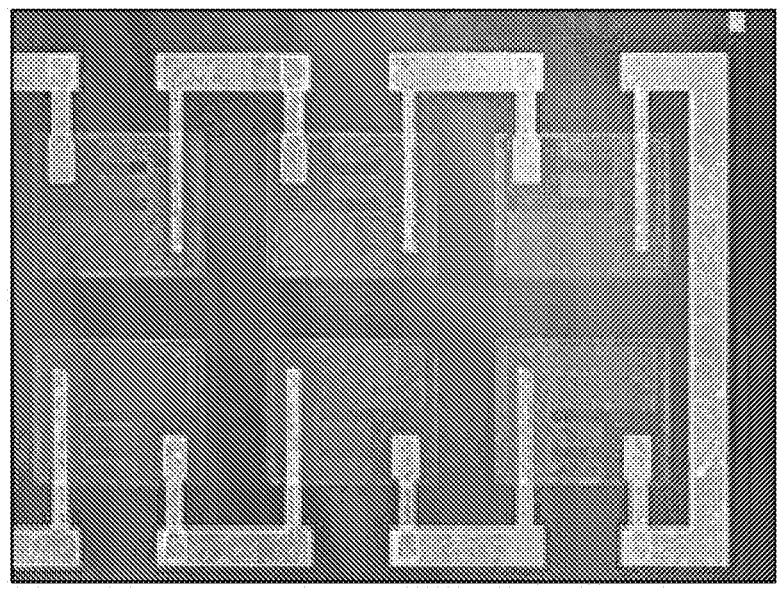
FIG. 17 illustrates a photographic image showing a six sensor unit device of a second generation, photolithographic design, according to an embodiment of the present invention.
Figure 18:
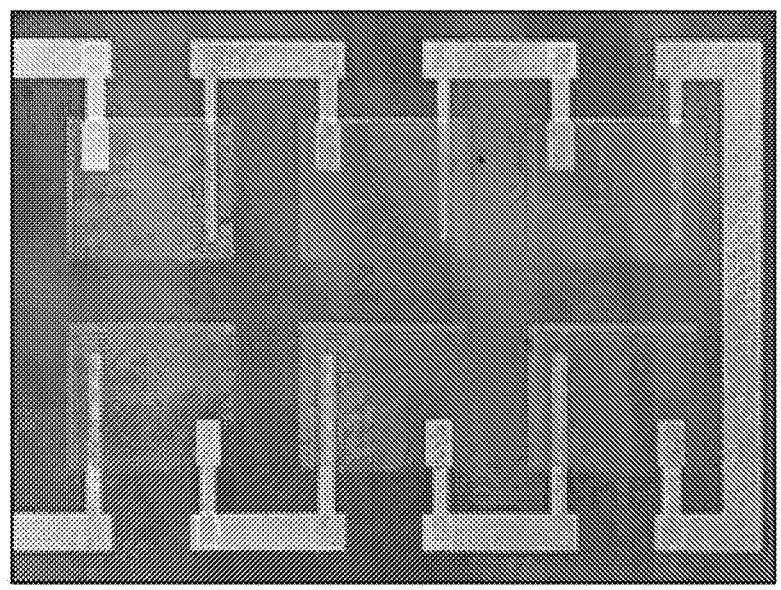
FIG. 18 illustrates a photographic image showing a six sensor unit device of an alternative second generation, photolithographic design, according to an embodiment of the present invention.
Figure 19A:
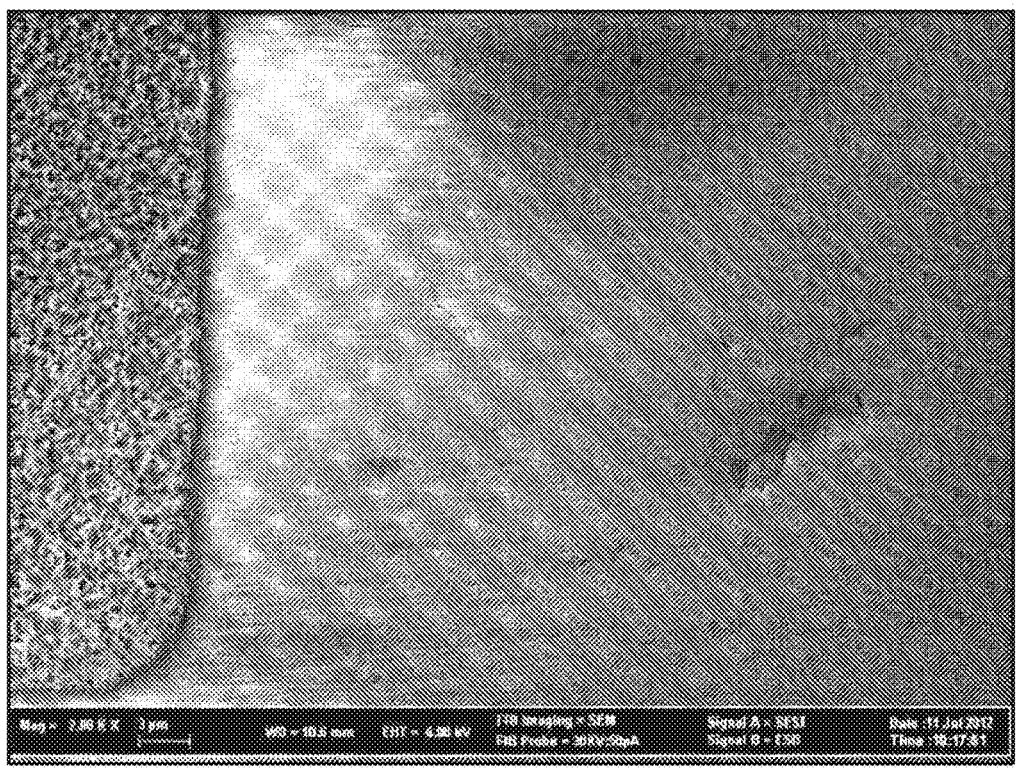
FIGS. 19a and 19b are SEM images of sensor showing cracks of the YSZ following the photolithographic process, according to an embodiment of the present invention.
Figure 19B:
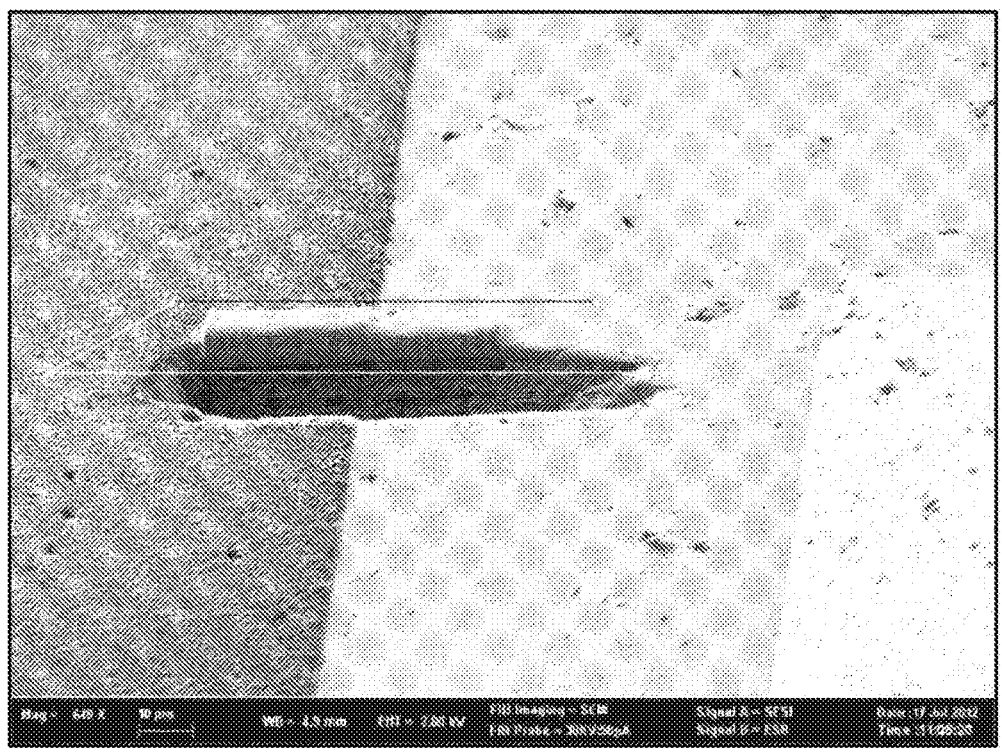
Figure 20:
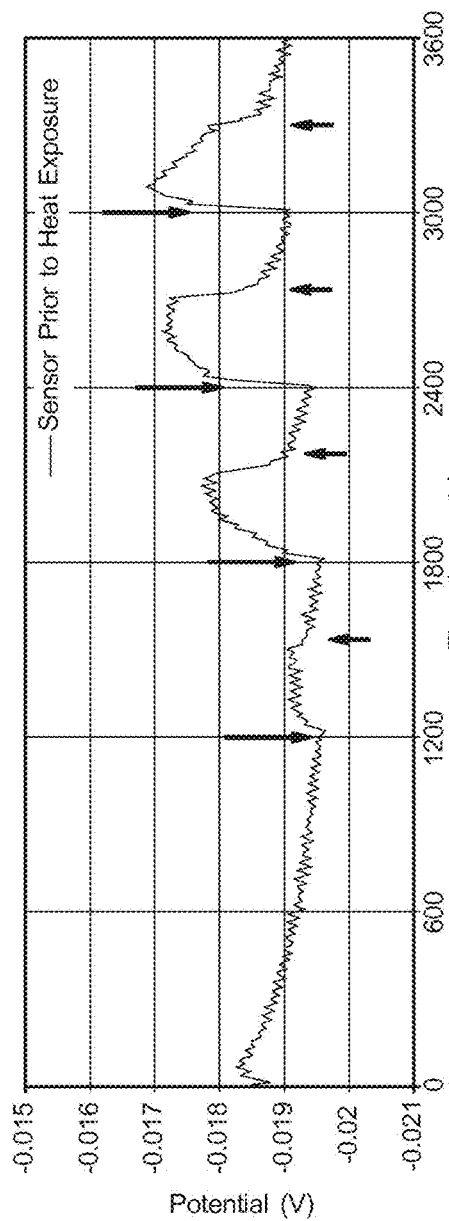
FIG. 20 illustrates a plot of test results of a sensor device before extended heat exposure, according to an embodiment of the present invention.
Figure 21:
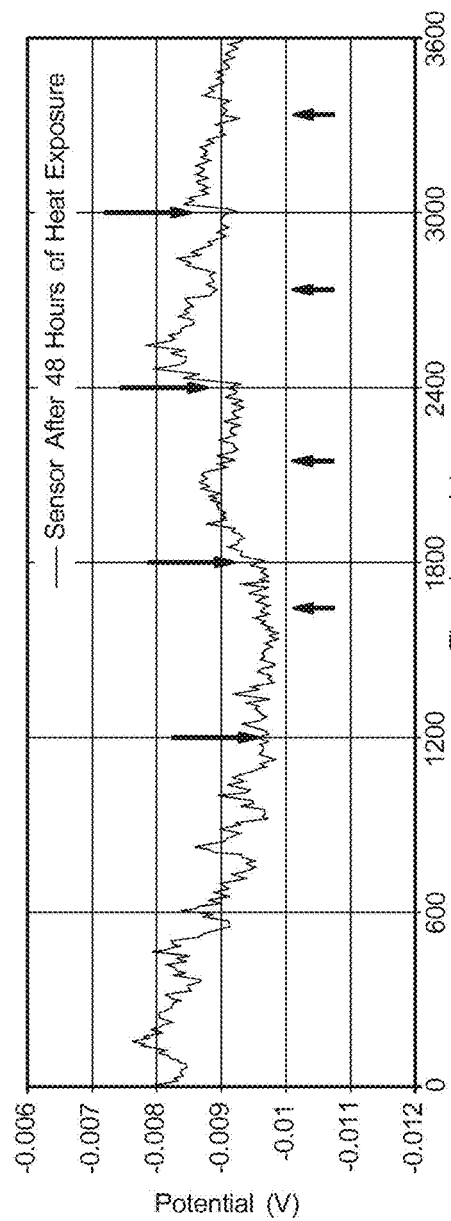
FIG. 21 illustrates a plot of test results after 48 hours of continuous heat exposure, according to an embodiment of the present invention.
Figure 22:
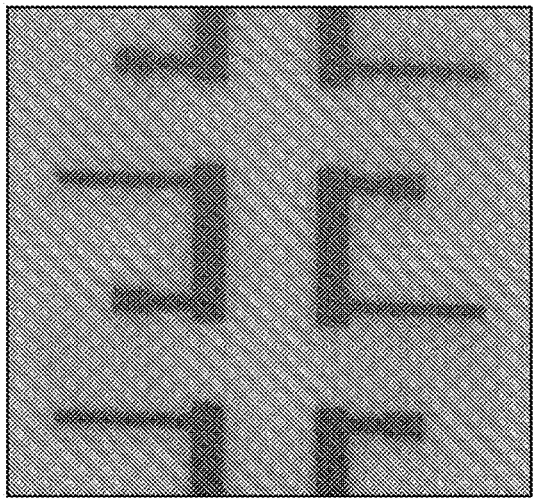
FIGS. 22 and 23 before and after, respectively, extended heat exposure, according to an embodiment of the present invention.
Figure 23:
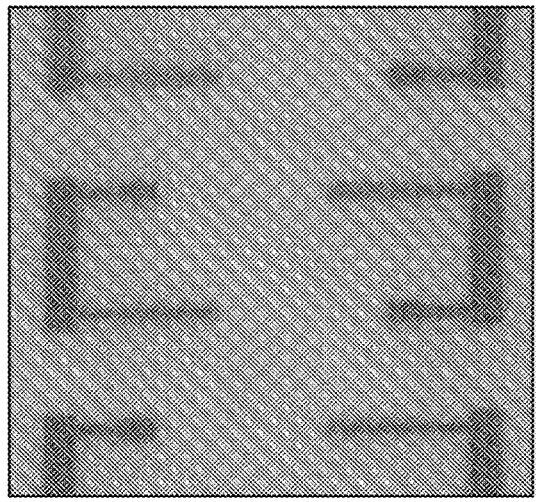
Figure 24A:
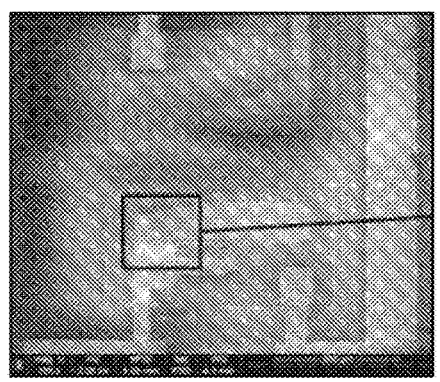
FIGS. 24a-d illustrate SEM images of sensor region containing WO3 after heat exposure, according to an embodiment of the present invention.
Figure 24B:
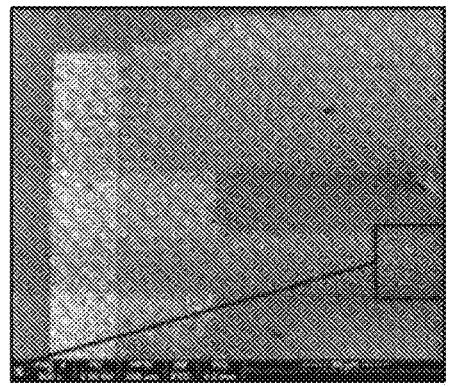
Figure 24C:
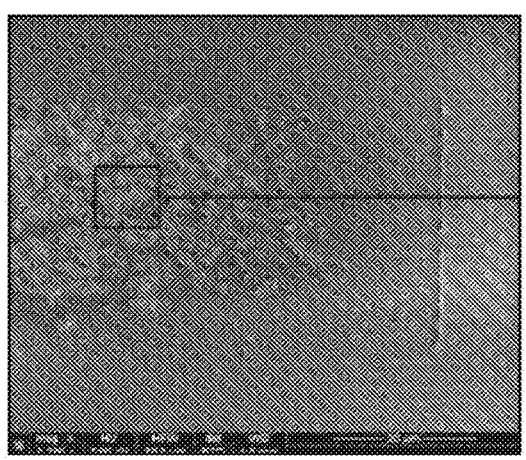
Figure 24D:
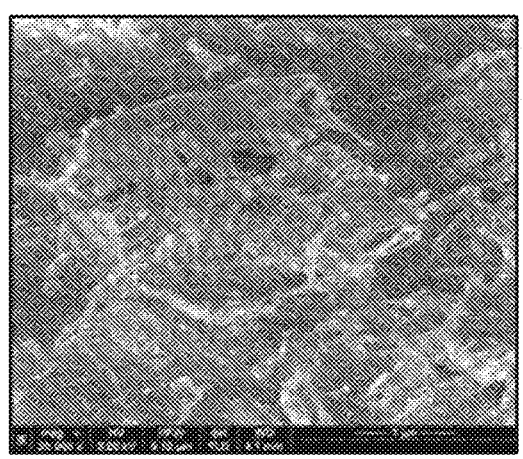

The results of the photoresist-based version are shown in FIG. 16. As can be seen in the test results, the photoresist-based version of the sensor array was capable of reaching below 500 ppb. These results are from a sensor array of 15 sensors connected in series on a chip. These sensors were tested using a catalytic filter to improve signal response and remove possible interfering gases.

The results of the testing on these various generations of designs indicate that the changes that were made between each generation were indeed beneficial to the overall performance of the sensor. Reducing the exposed Pt on the YSZ and increasing the WO3 covering the YSZ improved the sensitivity of the sensor as can be seen in comparing the results of the first and second generation shadow mask designs. The resulting design changes were applied to the photomask-based design, which is basically the second generation shadow mask design that was a factor of 0.35 in size compared to the shadow mask design. The test results of the photoresist design indicate that the sensor device is capable of at least 500 ppb level sensitivity and lower.

It was found during testing of the sensor arrays is the increased impedance of the connected connector array. In general, the 15 sensor array was found to be in the 60 MOhm range at operating temperature. The high impedance made the sensor array very sensitive to electrical Noise in the surrounding environment. A thicker YSZ film can decrease the impedance of the sensor due to the thicker film increasing the area through which ions could move from one end to the other of the sensor, however, it is found that the residual stress in the YSZ film increases and at higher thicknesses this stress can cause cracking in the film, especially after a thermal exertion to the operating temperature of the sensor. These cracks often run through the film, as seen in FIGS. 24a-24d, and could possibly result in lower conductivity of the film.

Another possible issue is the longevity of the sensors. Although the sensors were capable of repeated performance during testing it was found that over a longer period of time (several days of continuous testing) that the sensor performance would gradually decrease. From optical and SEM examination it appears that the films may be reacting at temperature and migrating from their original deposited locations.

Although the invention has been described with reference to several specific embodiments, this description is not meant to be construed in a limited sense. Various modifications of the disclosed embodiments, as well as alternative embodiments of the invention will become apparent to persons skilled in the art upon the reference to the description of the invention. It is, therefore, contemplated that the appended claims will cover such modifications that fall within the scope of the invention.

Having described the invention, we claim:

1. A microfabricated potentiometric gas sensor device comprising:
    a base substrate;
    an electrolyte layer disposed on the base substrate; and
    a plurality of potentiometric sensor units connected in series and coupled to the base substrate, each potentiometric sensor unit comprising:
        an electrolyte layer disposed on the base substrate;
        a two-part sensing electrode comprising a layer of tungsten oxide ($WO_3$) disposed on a platinum (Pt) contact; and
        a reference electrode comprising platinum (Pt);
    wherein the ratio of the surface area of the tungsten oxide ($WO_3$) of the sensing electrode disposed on the electrolyte to the surface area of the Pt of the reference electrode disposed on the electrolyte is at least 2 to 1.

2. The microfabricated potentiometric gas sensor device of claim 1, wherein the sensor device is a MEMS sensor device.

3. The microfabricated potentiometric gas sensor device of claim 1, wherein the sensor device is capable of determining the gas level at a sensitivity of at least 1 ppm.

4. The microfabricated potentiometric gas sensor device of claim 1, wherein the sensor device is capable of determining the gas level at a sensitivity of at least 500 ppb.

5. The microfabricated potentiometric gas sensor device of claim 1, wherein the sensor device is capable of determining the gas level at a sensitivity of at least 300 ppb.

6. The microfabricated potentiometric gas sensor device of claim 1, wherein the electrolyte comprises yttria-stabilized zirconia (YSZ).

7. The microfabricated potentiometric gas sensor device of claim 1, wherein the substrate comprises a material that is an insulator.

8. The microfabricated potentiometric gas sensor device of claim 1, wherein a thickness of the electrolyte layer is maximized a sufficient amount to minimize the internal resistance of the corresponding potentiometric sensor unit,
and such that the internal resistance of each of the plurality of potentiometric sensor units is minimized so as to minimize the overall resistance of the microfabricated potentiometric gas sensor device and increase sensitivity of the microfabricated potentiometric gas sensor device.

9. The microfabricated gas sensor device of claim 1, wherein the exposed surface of the electrolyte layer is minimized a sufficient amount to result in increased sensitivity of the microfabricated potentiometric gas sensor device.

10. The microfabricated gas sensor device of claim 1, wherein the electrolyte is YSZ and the surface area of the $WO_3$ sensing electrode on the electrolyte is fabricated using microfabrication techniques so as to maximize the ratio to that of the $WO_3$ to the Pt reference electrode on the electrolyte while minimizing the exposed layer of electrolyte layer.

11. The microfabricated gas sensor device of claim 1, wherein the ratio of the surface area of the $WO_3$ sensing electrode to the surface area of the Pt contact is sufficiently high to increase the sensitivity of the microfabricated potentiometric gas sensor device.

12. The microfabricated gas sensor device of claim 9, wherein the ratio of the surface area of the $WO_3$ sensing electrode to the surface area of the Pt contact is sufficiently high to increase the sensitivity of the microfabricated potentiometric gas sensor device.

13. The microfabricated sensor device of claim 12, wherein a thickness of the electrolyte layer of each sensor unit is maximized a sufficient amount to minimize the internal resistance of the corresponding potentiometric sensor unit,
and such that the internal resistance of each of the plurality of potentiometric sensor units is minimized so as to minimize the overall resistance of the microfabricated potentiometric gas sensor device and increase sensitivity of the microfabricated potentiometric gas sensor device.

14. The microfabricated potentiometric gas sensor device of claim 1, further comprising:
a first electrical interconnect coupled to the sensing electrode of a first potentiometric sensor within the series of potentiometric sensor units;
a second electrical interconnect electrically coupled to the reference electrode of a last potentiometric sensor within the series of potentiometric sensors; and
wherein the microfabricated potentiometric gas sensor device is capable of measuring a combined potential difference at the first and second electrical leads.

15. The microfabricated potentiometric gas sensor device of claim 14, further comprising a third potentiometric sensor unit electrically coupled between the first and last potentiometric sensor units within the series of potentiometric sensors,
wherein the sensing electrode of the first potentiometric sensor is connected to the reference electrode of the third potentiometric sensor.

16. The microfabricated potentiometric gas sensor device of claim 15, wherein the combined potential difference comprises a sum of the potential differences of the first, the second and the third potentiometric sensor units.

17. The microfabricated potentiometric gas sensor device of claim 1, wherein the sensor device comprises 15 to 20 sensor units.

18. A microfabricated potentiometric sensor device for detecting gas comprising:
a base substrate;
an electrolyte layer disposed on the base substrate; and
a plurality of potentiometric sensor units connected in series and couples to the base substrate, each potentiometric sensor unit comprising:
an electrolyte layer disposed on the base substrate;
a two-part sensing electrode comprising a layer of $WO_3$ disposed on a Pt contact; and
a reference electrode comprising Pt;
wherein the ratio of the surface area of the $WO_3$ sensing electrode disposed on the electrolyte to the surface area of the Pt reference electrode disposed on the electrolyte is sufficiently high such that the microfabricated potentiometric gas sensor device is capable of detecting the gas level at a sensitivity of at least 1 ppm.

19. The microfabricated potentiometric gas sensor device of claim 18, wherein the gas comprises $NO_x$.

20. The microfabricated potentiometric gas sensor device of claim 19, wherein the sensor device determines the gas level of $NO_x$ at a sensitivity of at least 300 ppb.

* * * * *